(12) United States Patent
Bergstrand et al.

(10) Patent No.: US 6,288,250 B1
(45) Date of Patent: Sep. 11, 2001

(54) COMPOUNDS

(75) Inventors: Håkan Bergstrand, Bjärred; Jan Dahmén, Åkarp; Bengt Särnstrand, Lund, all of (SE)

(73) Assignee: Astra Aktiebolag, Sodertalje (SE)

( * ) Notice: Subject to any disclaimer, the term of this patent is extended or adjusted under 35 U.S.C. 154(b) by 0 days.

(21) Appl. No.: 09/331,296

(22) PCT Filed: Mar. 16, 1999

(86) PCT No.: PCT/SE99/00415

§ 371 Date: Sep. 30, 1999

§ 102(e) Date: Sep. 30, 1999

(87) PCT Pub. No.: WO99/48865

PCT Pub. Date: Sep. 30, 1999

(30) Foreign Application Priority Data

Mar. 20, 1998 (SE) .................................................... 9800932

(51) Int. Cl.[7] ..................... C07C 231/00; C07C 233/00; C07C 235/00; C07C 237/00; C11C 3/00
(52) U.S. Cl. ................................ 554/42; 554/46; 554/47; 514/885; 514/824
(58) Field of Search .................. 554/42, 46, 47; 514/885, 824

(56) References Cited

FOREIGN PATENT DOCUMENTS

93/11104 * 11/1992 (WO).
93/11104 6/1993 (WO).
97/48679 12/1997 (WO).
98/12218 3/1998 (WO).

OTHER PUBLICATIONS

CAPLUS, Accession No. 1996:691489, Wlodek et al., "Selective Modulatio nof non-protein sulfhydryl levels in Ehrlich ascites tumor bearing mice", Neoplasma, 43(4) :259–263, 1996.
CAPLUS, Accession No. 1982:579303, Fellman et al., "Cysteine thiosulfonate in cysteine metabolism", Arch. Biochem. Biophys., 281(1) :303–308, 1982.

* cited by examiner

Primary Examiner—Johann Richter
Assistant Examiner—Diedra Faulkner
(74) Attorney, Agent, or Firm—Fish & Richardson P.C.

(57) ABSTRACT

Compounds of the general formula

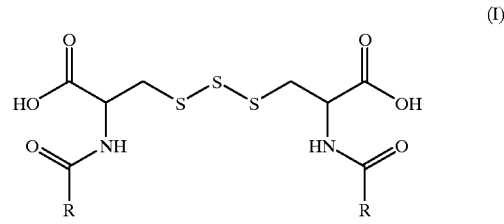

wherein R represents a straight or branched chain alkyl group containing from 1 to 16 carbon atoms, pharmaceutically acceptable salts thereof and/or optical isomers thereof have an immunostimulating effect, and are useful in the treatment of arteriosclerosis.

11 Claims, No Drawings

COMPOUNDS

This application is a 371 of PCT/SE99/00415 filed Mar. 16, 1999.

FIELD OF THE INVENTION

The invention provides new compounds, specifically novel trisulphides and salts thereof, processes for their preparation, compositions containing them and methods for their use.

BACKGROUND OF THE INVENTION

N-acetyl-L-cysteine is a well known compound which is routinely used as a therapeutic agent against chronic obstructive pulmonary diseases, particularly chronic bronchitis. The mode of action of the compound is not fully clarified but it is considered that the compound acts as a mycolytic agent or an antioxidant. Reduction of the degree of exacerbations in patients suffering from chronic bronchitis has been reported for N-acetyl-L-cysteine. A possible explanation for this effect could be that the compound enhances the host defence in these patents (see Bergstrand, H. et al J. Free Radic. Biol. Med. 2, 119–127, 1986).

The corresponding disulphide of N-acetyl-L-cysteine, N,N'-diacetylcystine (DiNAC), is a potent immunostimulator as revealed by its capacity to enhance a contact sensitivity reaction in mice.

DESCRIPTION OF THE INVENTION

According to the invention there is provided a compound of the general formula

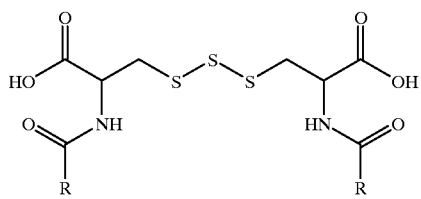

(I)

wherein R represents a straight or branched chain alkyl group containing from 1 to 16 carbon atoms, a pharmaceutically acceptable salt thereof and/or an optical isomer thereof.

Preferably R represents a methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, iso-propyl, 1-methylpropyl, tert-butyl, 2-methylbutyl or 3-methylbutyl group.

Examples of pharmaceutically acceptable salts of compounds according to the invention include the sodium, potassium, calcium, magnesium or ammonium salt or salts of mono- or di-protonated organic amines such as lysine, ethylenediamine, N,N'-dibenzyl ethylenediamine, adamantanamine, N-benzyl-2-phenylethylamine, benzathine, chloroprocaine, choline, diethanolamine, meglumine, procaine, benethamine, clemizole, tromethamine, ethanolamine, 2-amino-2-methyl-1,3-propanediol, tert. butylamine, triethanolamine, pyridoxine, nicotineamide, methyl nicotinate, arginine, histidine, morpholine, N-methylpiperidine, spermine, sperimidine, cysteamine, cystamine, metheneamine, piperazine.

The compound according to the invention may optionally be in the form of a racemic mixture or of the D,D- or L,L-isomer or meso form. It is preferably in the form of its L,L-isomer.

According to the invention there is further provided a process for the preparation of a compound of formula (I) which comprises reacting a compound of formula (II)

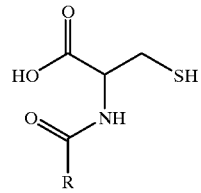

(II)

wherein R is as defined above, with a sulphur transferring coupling agent, and, optionally, reacting the product obtained with a suitable base to obtain a pharmaceutically acceptable salt, and/or isolating an optical isomer.

Suitable sulphur transferring coupling agents used in the process according to the invention include N,N'-thio-bis (phthalimide), N,N'-dibenzimidazyl sulphide, thiobis (imidazole), sulphur dichloride, sulphur momochloride, elemental sulphur, preferably, N,N'-thio-bis(phthalimide).

The process according to the invention is preferably carried out in a polar solvent, more preferably in a mixture of water and a polar organic solvent. Examples of suitable polar organic solvents include n-propanol, isopropanol, ethanol, buthanol, aceton, tetrahydrofuran and/or acetonitrile. A mixture of water and isopropanol is particularly preferred.

The isolation of optical isomers can be carried out using conventional methods.

The compound of formula (II) can be prepared from commercially available starting materials using methods known to a person of skill in the art.

According to the invention there is also provided a pharmaceutical composition comprising a compound of formula (I) in association with a pharmaceutically acceptable carrier and/or excipient. The composition according to the invention is optionally formulated in a manner suitable for administration by inhalation, or for oral, topical or parenteral administration. The composition may optionally be in the form of, for example, an aerosol, tablet, coated tablet, gelatine capsule or a solution, as appropriate.

For the preparation of a tablet, coated tablet or gelatine capsule, a compound according to the invention is combined with a suitable pharmaceutically acceptable carrier such as lactose, starch, dicalcium phosphate, microcrystalline cellulose, polyvinylpyrrolidone, gelatine, cellulose derivatives, colloidal silicone dioxide, talc and/or stearic acid and/or a salt thereof.

For the preparation of a solution, a compound according to the invention is combined with a pharmaceutically acceptable excipient such as water, saccharose, glucose, sorbitol, fructose and/or xylitol.

The pharmaceutical composition according to the invention may optionally further comprise a preservative, stabiliser, viscosity regulating agent, emulsifier, sweetening agent, colouring agent, flavouring agent, tonicity regulating agent, buffer and/or an oxidant. It may optionally also comprise another therapeutically active substance.

The invention provides compounds for use in medical therapy, especially compounds with advantageous properties for the treatment of diseases, particularly diseases where an anergy of the immune response or an aberrant immune response or an ineffective host defence is expected. Such diseases include chronic bronchitis, where a reduction of the rate of exacerbations has previously been reported with immune response modifiers such as Biostim® (Radermecker, M. et al. Int. J. Immunopharmac. 10, 913–917, 1988; Scheffer, J. et al. Arzneim Forsch/Drug Res. 41, 815–820, 1991), Ribomunyl® and BronchoVaxom (Paupe, J. Respiration 58, 150–154, 1991) as well as with N-acetylcysteine (Bergstrand, H. et al J. Free Radic. Biol. Med. 2, 119–127, 1986).

Diseases which the compounds of the invention can be used to treat include certain forms of malignant diseases. There are numerous reviews in the literature concerning ways of stimulating the immune response in patients with various forms of malignant diseases (Stevenson, F. K. FASEB J 5: 2250–2257, 1991; Melief, C. J. M. Advances in Cancer Research 58: 143–75, 1992; Chen, J. et al., Immunology Today 14:10, 483–86, 1993). For example patients with intracranial tumours (gliomas) exhibit a profound decrease in immunity possibly due to a defect in the secretion of IL-2 as well as the expression of IL-2 receptors in T cells from these patients (Roszman, T. et al. Immunology Today 12, 370–374, 1991). A significant adjuvant effect in immunotherapy of melanoma and colon carcinoma has been documented for the immunostimulator Levamisole (Van Wauwe, J. and Janssen, P. A. J: Int J. Immunopharmac. 13, 3–9, 1991). Also immunotherapy with IL-2 in vivo or treatment of patients' lymphokine activated killer cells with IL-2 ex vivo has caused the regression of cancer (Rosenberg, S. A. Immunology Today 9, 58–62, 1988).

The malignant diseases for which the compounds of the invention are expected to have advantageous effects include tumours of mesenchymal origin such as sarcomas like fibrosarcoma, myxosarcoma, liposarcoma, chondrosarcoma, osteogenic sarcoma or chordosarcoma, sarcomas like angiosarcoma, endotheliosarcoma, lymphangiosarcoma, synoviosarcoma or mesotheliosarcoma, leukemias and lymphomas like granulocytic leukemia, monocytic leukemia, lymphocytic leukemia, malignant lymphoma, plasmocytoma, reticulum cell sarcoma or Hodgkins disease, sarcomas like leiomysarcoma or rhabdomysarcoma, tumours of epithelial origin (carcinomas) like squamous cell carcinoma, basal cell carcinoma, sweat gland carcinoma, sebaceous gland carcinoma, adenocarcinoma, papillary carcinoma, papillary adenocarcinoma, cystadenocarcinoma, medullary carcinoma, undifferentiated carcinoma, bronchogenic carcinoma, melanoma, renal cell carcinoma, hepatoma-liver cell carcinoma, bile duct carcinoma-cholangiocarcinoma, papillary carcinoma, transitional cell carcinoma, squamous cell carcinoma, choriocarcinoma, semonoma or embryonal carcinoma, tumours of the central nervous system like glioma, meningoma, medulloblastoma, schwannoma or ependymoma.

Moreover, the compounds according to the present invention also have advantageous properties for the treatment of chronic infections such as herpes, aphtous stomatitis and minimal change syndrome where clinical improvement has previously been reported by treatment with an immuno-stimulator such as Levamisole, other chronic inflammatory diseases in the urinary tract or in ear, nose or throat, which benefit from treatment with immunostimulators such as Biostim®, Broncho-Vaxom and Ribomunyl® and HIV infection or AIDS.

Moreover, an impairment, a defect or an imbalance of the immune response has also been postulated to exist at atopic diseases such as atopic dermatitis, rhinitis and asthma (Katz, D. H. Immunology Rewiews 41, 77–108, 1977). Since theoretical considerations suggest that stimulation of an immune response would possibly be the best way of restoring imbalances and auto-immunity (Varela, F. J. and Coutinho, A. Immunology Today 12, 159–166, 1991), the compounds of the invention are also expected to have advantageous properties for the treatment of asthma, rhinitis, atopic dermatitis and autoimmune diseases like non-obese diabetes, systemic lupus erythematosus, sclerodermia, Sjögren's syndrome, dermatomyositis or multiple sclerosis, rheumatoid arthritis and psoriasis.

Moreover, the compounds according to the present invention, due to their immunostimulating properties, are believed to have advantageous properties as adjuvants in various forms of vaccine preparations. Due to their immunomodulating properties, the compounds according to the invention are also expected to have favourable properties in inhibiting rejection of transplanted organs.

Finally, the compounds according to the present invention are expected to have advantageous properties in the treatment of arteriosclerosis (Hansson. G. K. et al. Proc. Nat. Acad. Sci. USA 88, 10530, 1991).

The compounds according to the present invention are particularly suitable for treatment of malignancies such as melanoma, mammary carcinoma, gastrointestinal carcinoma, glioma, bladder carcinoma and squamous cell carcinoma of the neck and head region;

diseases in the respiratory tract such as chronic bronchitis, asthma, rhinitis:

atopic diseases such as atopic dermatitis;

infections such as hepatitis, post-infectious anergy and aquired immune deficiencies such as AIDS;

posttraumatic immunological anergy; and purported autoimmune diseases such as rheumatoid arthritis, multiple sclerosis, artherioscierosis and psoriasis.

A further object of the invention is the use of the compounds of the present invention in the manufacture of a medicament with immunostimulating effect and especially of medicament for the treatment of arteriosclerosis.

Another object of the invention is a method of immunostimulation, which comprises administrering to a host in need of such treatment an effective amount of the compound of the present invention.

Another object of the invention is a method for treatment of arteriosclerosis which comprises administrering to a host in need of such treatment an effective amount of the compound of the present invention.

The invention is illustrated by the following example which should not be interpreted as limiting the scope of the invention.

EXAMPLE (R,R')-3,3'-trithiobis-2-acetamidopropanoic acid [N, N'-diacetyl-L-cystine trisulphide (acid form)]

N-acetylcysteine (5 g, 30.6 mmol) was suspended in a mixture of isopropanol and water (1:1, 3.0 L) and N,N'-thio-bis(phthalimide) (5 g, 15.4 mmol) was added. The mixture was stirred at ambient temperature for 24 h, after which time the clear solution was evaporated free from isopropanol. Filtration of precipitated material, followed by freeze drying gave the crude trisulphide product, contaminated by phthalimide as the major impurity. Preparative HPLC [Kromasil K100-10-C18 column (2"×250 mm) using acetonitrile/water (19/81), containing 0.1% trifluoroacetic acid, as eluent at a flow rate of 40 mL/min and detection at 220 nm] gave after freeze drying, the pure title compound in quantitative yield M+H: 357.

Pharmacological Test

The ability of the compounds of the invention to modulate immune responses was confirmed using the following animal delayed type hyper-sensitivity (DTH) test in the mouse.

Both male and female Balb/c mice having a weight of from 18 to 20 grams obtained from Bomholtsgaard (Denmark) were used. 4-Ethoxymethylene-2-phenyloxazolin-5-one (OXA, purchased from BDH, England) was used as the antigen in this test.

The mice were sensitised, Day 0, by epicutaneous application of 150 ml of an absolute ethanol-acetone (3:1) solution containing 3% OXA on the shaved abdomen. Treatment with a compound according to the invention or vehicle (0.9% NaCl) was initiated by oral feeding immediately after sensitisation and continued once daily until Day 6. Seven days (Day 6) after the sensitisation, both ears of all mice were challenged on both sides by topical application of 20 ml 1% OXA dissolved in peanut oil. Ear thickness was measured prior to and 24 or 48 hours after challenge using an Oditest spring calliper. Challenges and measurements were performed under light pentobarbital anaesthesia.

The intensity of the DTH reactions was expressed according to the formula: Tt24/48-Tt0 mm units, where t0, t24 and t48 represent the ear thickness before and 24 or 48 hours after challenge respectively, in individual tests (T). The results were expressed as the mean±S.E.M. The level of significance between means of the groups was obtained by Student's two-tailed t-test. The immunostimulating potency of the compound was measured by comparing the increase in ear thickness with that obtained in the control.

What is claimed is:

1. A compound of the general formula

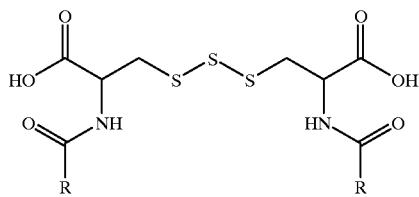

(I)

wherein R represents a straight or branched chain alkyl group containing from 1 to 16 carbon atoms, a pharmaceutically acceptable salt thereof and/or an optical isomer thereof.

2. A compound according to claim 1 wherein R represents a methyl, ethyl, n-propyl, n-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, isopropyl, 1-methylpropyl, tert-butyl, 2-methylbutyl or 3-methylbutyl group.

3. A prrocess for the preparation of a compound as defined in claim 1, which process comprises reacting a commpound of formula (II)

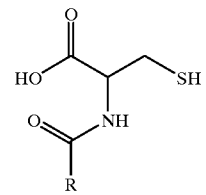

(II)

wherein R is as defined in claim 1, with a sulphur transferring coupling agent; and, optionally, reacting the product obtained with a suitable base to obtain a pharmaceutically acceptable salt, and/or isolating an optical isomer.

4. A process according to claim 3 wherein the sulphur transferring coupling agent is N,N'-thio-bis(phthalimide).

5. A pharmaceutical composition comprising a compound as defined in claim 1 in association with a pharmaceutically acceptable carrier and/or excipient.

6. A method for immunostimulation, which comprises administering to a host in need of immunostimulation an effective amount of a compound as defined in claim 1.

7. A method for the treatment of arteriosclerosis, which comprises administering to a host in need of such treatment an effective amount of a compound as defined in claim 1.

8. A method for immunostimulation, which comprises administering to a host in need of immunostimulation an effective amount of a composition as defined in claim 5.

9. A method for the treatment of arteriosclerosis, which comprises administering to a host in need of such treatment an effective amount of a composition as defined in claim 5.

10. A method for immunostimulation, which comprises administering to a host in need of immunostimulation an effective amount of a compound as defined in claim 2.

11. A method for treating arteriosclerosis which comprises administering to a host in need of such treatment an effective amount of a compound as defined in claim 2.

* * * * *